United States Patent [19]

McFarlane

[11] 4,046,144

[45] Sept. 6, 1977

[54] CATHETER PLACEMENT ASSEMBLY

[76] Inventor: Richard H. McFarlane, 2571 Kaneville Court, Geneva, Ill. 60134

[21] Appl. No.: 614,707

[22] Filed: Sept. 18, 1975

[51] Int. Cl.$^2$ .......................................... A61M 25/00
[52] U.S. Cl. ................................. 128/214.4; 128/221; 128/DIG. 16
[58] Field of Search ............ 128/221, DIG. 16, 214.4, 128/347, 348, 214 R

[56] References Cited

U.S. PATENT DOCUMENTS

| | | | |
|---|---|---|---|
| 3,157,481 | 11/1964 | Bujan | 128/221 X |
| 3,352,622 | 11/1967 | Schachter | 401/141 |
| 3,714,945 | 2/1973 | Stanley | 128/214.4 |
| 3,727,613 | 4/1973 | Sorenson et al. | 128/221 X |
| 3,734,095 | 5/1973 | Santomieri | 128/214.4 |
| 3,851,647 | 12/1974 | Monestere et al. | 128/214.4 |
| 3,854,907 | 12/1974 | Rising | 128/214 R X |
| 3,896,733 | 7/1975 | Rosenberg | 128/214 R |

Primary Examiner—Stephen C. Pellegrino

[57] ABSTRACT

An improved catheter placement assembly which includes an improved rigid needle and hub assembly and an improved catheter assembly with a flexible cannula jacketing the needle shank and a flexible body of rubbery material on its proximal end with a rigid adapter to connect to an I.V. set; the hub assembly of the needle defines a chamber to protectively house the adapter connection zone during venipuncture.

12 Claims, 6 Drawing Figures

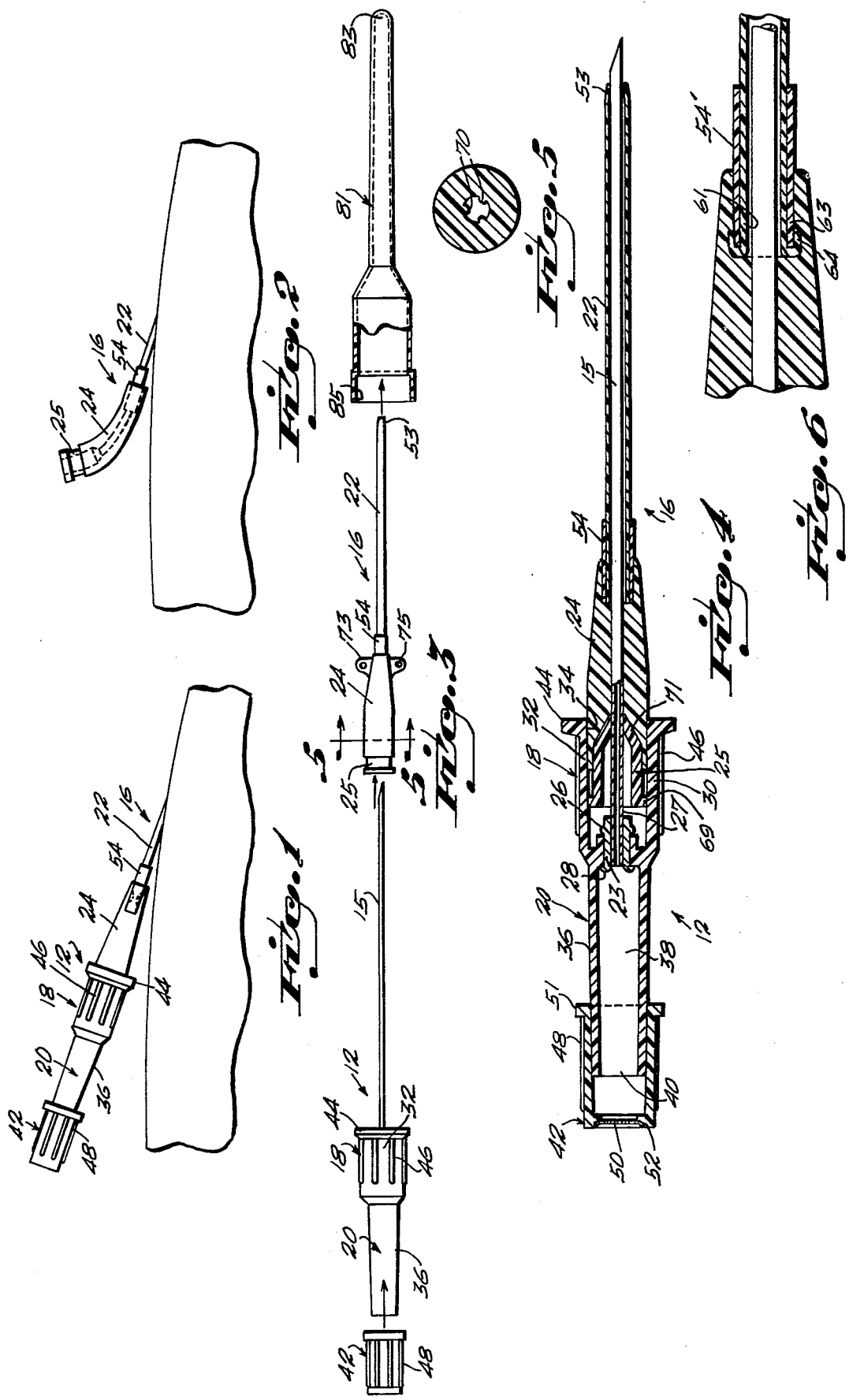

CATHETER PLACEMENT ASSEMBLY

FIELD OF THE INVENTION

This invention relates to an improved catheter placement assembly, and, more particularly, to an improved needle construction and to an improved catheter structure and combination of the same in the placement assembly.

BACKGROUND OF THE INVENTION

In the past, there have been numerous types of catheters which are flexible and which are provided with rigid adapters on one end to connect to a medical device, for example, a tubing for intervenous feeding, etc., after a rigid needle or stylet has been removed from within it following a venipuncture operation.

Generally, the present invention in one form is of an improved catheter and needle assembly which includes a catheter having a generally tubular body or housing intermediate the adapter and catheter proper which body is formed of a flexible and bendable rubbery material. Among the improvements is structure within the lumen of the tubular body or housing which projects into the lumen or passageway so that upon bending, flexing or external application of pressure, the lumen through the body or housing is not completely occluded and flow is not completely blocked.

The present invention also includes structure which accomplishes the following objects:

It is also an object of this invention to provide an improved catheter placement assembly which includes a needle with a hub fixed to the proximal end zone which includes a distally-extending axially-opening hood or skirt to define an annular chamber to protectively house the mouth or lure of the adapter to avoid contamination of it by removing the fingers from the lure's edge or lip while the placement assembly is manipulated during a venipuncture operation.

It is another object of this invention to provide an improved catheter which includes a housing or generally tubular body on the proximal end of the catheter which is of rubbery material so that it may be easily manipulated and which is of a sufficient axial length to provide adequate handling room to advance the catheter along the needle while the catheter is being inserted to avoid contamination of the lure edge or lip as it is withdrawn from the protective housing within the skirt of the needle hub.

It is another object of this invention to provide an improved housing between the catheter proper and the adapter so that the proximal end of the catheter housing can be easily manipulated to orient the adapter at a favorable angle for connection to a tubing of an intravenous set, for example, FIG. 2.

It is another object of this invention to provide an improved catheter and needle assembly which includes a flash back chamber so that upon introduction of the needle into a vein there will be a flow of blood into the chamber and therapist can visually observe that the tip of the needle is in the correct position within a vein.

It is also an object of this invention to provide an improved device which includes a vent means to permit air, but not blood, to escape from the flash back chamber in response to blood pressure on venipuncture; thus, the pressure does not build up and stop blood flow into the chamber.

It is a further object of this invention to provide an improved catheter with radially outwardly projecting surfaces on the housing which are sized and positioned to adapt it to be readily taped in position and which stabilize the unit once in position.

It is also an object of this invention to provide a catheter with an improved housing of soft rubbery material which is adapted to be manipulated without closing the flow path through it and yet which can be manipulated to reduce the amount of blood flow through it without permitting an accidental occlusion.

It is a further object of this invention to provide a catheter which has a flexible body or housing at the proximal end which is of bendable or rubbery material so that it is not only comfortable but can be easily bowed away from the skin surface to provide clearance for manipulating it to connect to tubes, etc., as is often required.

It is also an object of this invention to provide a catheter placement assembly which includes a flexible catheter sheathing a needle, which catheter includes a tubular body or housing at its proximal end, which housing is of a first axial length and with an adapter on the proximal end to connect to a medical device, and which needle includes a hub with an axially-facing, distally-opening skirt defining an annular chamber of a depth of a second predetermined length which is less than that of the first axial length and which is sized companionately to the adapter to protectively house the end thereof within the skirt during venipuncture so that it is not contaminated.

In accordance with these and other objects which will become apparent from the following description is of a preferred embodiment of the invention which is shown in a suitable size in FIG. 3.

DESCRIPTION OF THE DRAWINGS:

FIG. 1 is a partial view illustrating the catheter inserted and in use with a cap closing the end of the luer;

FIG. 2 is a view similar to FIG. 1 and illustrating the flexible rubbery body of the housing of the catheter;

FIG. 3 is an exploded view which is partly in cross section to illustrate the arrangement of the parts of the improved catheter assembly;

FIG. 4 is a view in cross section taken on the longitudinal centerline of the improved catheter in an assembled condition.

FIG. 5 is a view in cross section taken along the plane indicated by the line 5—5 of FIG. 3 and looking in the direction of the arrows; and FIG. 6 is a view in cross section of an alternative embodiment of the invention and illustrating the needle and housing connection in an alternative form to that shown in the central zone of FIG. 4.

DESCRIPTION OF PREFERRED EMBODIMENT

Referring to the drawings, wherein like reference characters designate like or corresponding parts throughout the several views, and referring particularly to FIG. 4, there is shown what is often termed in the art a catheter placement assembly. It is composed of two main portions: (a) a needle and hub assembly 12 and (b) a catheter or cannula assembly 16.

Generally speaking, the needle and hub assembly 12 comprises a hollow elongate pointed needle 15 with a hub 18 fixed to the proximal end, and which is structured to define a proximally located flash chamber or blood reservoir 20. The cannula assembly 16 comprises a tubular elongate, flexible needle cannula, catheter or sheath 22 sized to receive and jacket the main length of the needle 15 and a proximally located yieldable body or housing 24 of rubbery material on it which in turn is provided with an annular adapter 25 on the end which is sized to nest removably within a protective hood extending axially from the needle hub when the two main portions are assembled as a catheter placement assembly.

Referring in more detail to the first main portion, the needle and hub assembly 12, it comprises a conventional, hollow, distally-pointed, elongate needle or rigid stylet 15 connected to a hub 18 by conventional means. The means to connect may include a tubular fitting 23 fixed to the proximal end zone 26 of the needle, the proximal end or the or distal first end being designated by the numeral 26 and second end being designated by the numeral 28. The means to connect is radially outturned or upset to engage shoulder formed in the central zone of the hub to captivate the needle against axial movement of withdrawal or separation of it from a central axial bore through the hub 18.

The body of the hub includes the central zone 30 with the aforementioned through bore and a distally and axially extending hood or skirt 32 spaced from the needle shank defining an axially-opening annular receptacle 34. The hub body also includes a proximally-extending tapered, i.e., generally truncated conical, wall 36 defining an internal flash chamber 38 which terminates in an open mouth 40 that is closed by a removable cap means 42. The forward or distal end of the skirt 32 is provided with an out-turned rim means 44 to facilitate axial movement of the catheter placement assembly during venipuncture; and the exterior surface of this skirt may include gripping means in the form of knurling or radially-extending fins 46. The rear cap means 42, which closes the end of the flash chamber, is provided with tapered walls which correspondingly mate with the taper of the wall 36. The exterior surfaces of the end cap may also be provided with grip means or knurling as at 48 to rotatingly manipulate the same.

The flash chamber is preferably vented by suitable vent means. In the preferred embodiment a filter disk 50 is secured by suitable means in spanning relation of an opening through the end 52 of the cap. In a preferred embodiment, the filter disk is of bacteriological filter material through which air may pass, but the blood components cannot readily pass. Thus a disk may be conveniently made with the commercially available material known as, TYVEK, a trademark of the duPont Company; it consists of a thin sheet of polyethylene fibers in mat form which material has the quality of allowing air to escape but not blood. In a preferred embodiment, the disk 50 is suitably secured in spanning relation of the open ended cap and may be bonded to the material of the end cap by heat means to fuse the margin of the disk to the wall of the end cap about the opening. In the preferred embodiment the exterior of the end cap is provided with a radial flange 51 or rim to serve as a gripping means for removal of the end cap to connect to another medical device, the wall 36 serving as a fitting or connector means.

The cannula assembly 16 includes a flexible catheter sheathing the needle, such as a length of Teflon, a trademark of the duPont Company, to completely jacket or sheath a companionately sized needle from the flexible housing to the beveled needle point proper. Preferably the catheter end 53 is feathered or tapered to the needle surface at the proximal zone of the needle point proper for ease in entering on venipuncture. The venipuncture is produced by the needle, which is removably sheathed within the catheter and which has a sharp, tapered, penetrating tip projecting in advance of the leading end or feathered end of the catheter. In the preferred embodiment, the proximal end zone of the cannula or catheter tube is secured to the housing which is of yieldable or rubbery material. Retention means 54 interconnect the proximal end of the catheter in fluid communication with the interior of the housing to which it is fixed. The retention means may comprise a short, tubular segment or hinge joint of rigid, plastic material telescoped over the end of the cannula and bonded to or vulcanized to the rubbery material of the housing. The segment is fixed to the end zone of the catheter as by a tight fit, see FIG. 4. Alternatively, as in FIG. 6, where, for example, the catheter or cannula is of Teflon, the retention means 54' may comprise a tubular segment with the proximal end 61 of the Teflon passed through it and turned back on itself as at 64 over the end zone 63 to form a mechanical lock against axial movement supplemented by a bond between the rubbery material which is in effect vulcanized to the rigid plastic segment. To the proximal end of the rubbery housing, the adapter is connected. The exterior of the adapter is sized and is receivable and nestable snugly, yet removably, within the skirt of the hub. The skirt is preferably interiorly tapered to seat a rigid rim 69 and to limit axial movement of the rim 69 into the skirt thus serving as stop means for the catheter and means to orient the feathered end at the needle tip zone. Preferably, the rim 69 is square as seen in cross section and viewed axially. Within the longitudinally-extending bore of the housing, as shown in FIG. 5, longitudinally-extending ribs are provided which prevent occlusion of the longitudinally-extending passageway when the housing is flexed as shown in FIG. 2 or when external pressure is applied to the housing.

The overall sizing of a preferred embodiment is as shown in FIG. 3 of the drawing, which is to size. This size provides a relatively large flash chamber of about one-eighth inch in diameter and of about one inch in axial length so that visual observation can be made readily of blood in the flash chamber through the translucent wall to signal that the tip is properly in the vein. In the preferred embodiment, the hub of the needle and the adapter and the retention means are of molded plastic in the rigid range, for example, polypropylene. The rubbery material of a preferred embodiment of the housing of the cannula is of moldable Kraton, a product of the Shell Oil Company. The rubbery material should be such that, as shown in FIG. 2, flexing of the cannula housing is possible for manipulating it for most favorable orientation of the adapter end or lure to facilitate connection to tubing or another medical device. Because it is relatively soft it is comfortable when in place for long periods of time. The rubbery material of the body or housing of the preferred embodiment is bonded or vulcanized by heat to the adapter and to the retention means, the latter being effective to lock the cannula to the body as explained above for positive connection. Preferably the adapter is provided with a distalmost annular and symmetrical, axial nose 71 which projects into the through bore of the housing as shown. Further, stabilizing wings or ears such as 73 are provided on the exterior surface of the distal end of the cannula housing to provide stability against rolling and provide means for connecting the cannula by tape to the body of a patient when properly positioned. A weakened zone as shown at the tip of the arrow 75 may be provided in each ear to anchor it in place by sutures.

Preferably, an elongate protector shroud 81 of rigid plastic is provided which is closed at one end 83 and is open at the other end 85 and is sized to receive the rim of the hub of the needle to suspend it in protective relation within the elongate shroud prior to use. The wall of the shroud adjacent the open end 85 is inwardly tapered desirably and it includes a shoulder which abuts the rim 44 when assembled which serves as a stop means to limit penetration of the needle into the protector shroud.

For use, the protector is first removed from the catheter and needle assembly. The venipuncture operation is performed in the usual manner. The hub, which is of sufficient axial length to manipulate it conveniently is grasped about the skirt which protectively houses the end or rim 69 of the catheter adapter about the opening. When the vein has been punctured, blood will flow through the hollow needle and into the flashback chamber. Then, by handling the exposed portion of the flexible catheter body, see the zone indicated by the numeral 24, the catheter is advanced until it reaches the desired position in the vein, while the needle assembly is held in a relatively fixed position by continuing to grasp the hub. It will be seen that the fingers do not contaminate the proximal opening of the adapter in so doing. After this has been accomplished, the needle is completely removed. The end of a tube of an I.V. set is then connected to the rim of the adapter of the catheter. Finally, using a sling type taping, the catheter is anchored into position or otherwise anchored in place.

As shown in FIG. 3, the axial length of the rubbery material of the tubular catheter body or housing is greater than one-half inch and is preferably not longer than one inch, while, as seen in cross section, it has an outside diameter of about one-quarter of an inch between the center and proximal end and is provided with a through bore of about one-eighth of an inch so as to have a substantial mass and resistance to buckling in response to axial force application. Preferably, the stabilizing wings are of the same rubbery material as the catheter body. The catheter body or housing comprises a readily bowable or bendable member while the tubular retention means 54 and 54', which is rigid, serves as a hinge means element between the relatively flexible material of the cannula and the bendable body. The axial depth of the chamber in the skirt of the needle hub, between its open mouth and the stop means, determines the protected location of the opening into the adapter on the proximal end of the catheter; preferably this is at least one-quarter inch and between one-quarter inch and one-half inch. The axial length of the gripping area of the skirt, that is, between the rim and the flash chamber, is about one-half inch and between one-quarter and three-quarters of an inch.

It is thus seen that the device provides a protective annular chamber within the skirt of the needle hub which protectively houses the proximal end or mouth of the cannula during the venipuncture operation; and that the exterior of the skirt may be gripped to hold the needle in position while the cannula is advanced by gripping the portion of the flexible rubbery body extending from the mouth of the skirt and advancing the catheter in the vein relative to the needle point for proper positioning. When the needle is removed, the end of the catheter assembly can be bowed upwardly as shown in FIG. 2 for connection to another medical device, such as a tube, for intravenous feeding.

What is claimed is:

1. An improved catheter comprising, an axially aligned combination of
   a hollow, rigid, elongate needle with a pointed distal end and a proximal end zone, and
   a hub of rigid plastic material with a central zone secured about the proximal end zone of the needle,
   said central hub zone having a distally-extending generally cylindrical skirt spaced from said needle defining an annular, distally opening, axially extending chamber with an exterior surface and said hub including an annular shoulder intermediate the end zones and forming a partial annular end wall of the chamber, and
   said central hub zone having a proximally extending tubular wall defining a proximally opening flash chamber, the proximal end zone of said needle being in fluid communication with said flash chamber, and
   a vented removable cap closing said flash chamber,
   said distally opening chamber defining a mouth of said chamber in said hub with said hub being provided with rim means extending outwardly of said mouth and said rim means and exterior surface providing means to facilitate axial movement of advancement of the needle in a distal direction,
   said improved catheter including a thin, flexible elongate jacket having a proximal end and a distal end snugly jacketing the needle from the zone of the pointed distal end along the intermediate length of the needle and including a rigid adapter having a first end zone and a second end and means fixedly connecting the first end zone of the adapter to the jacket, said adapter being sized for snug receipt within said skirt protectively within said chamber with said second end normally in abutting engagement with the end wall of said chamber.

2. The devices as set forth in claim 1 wherein said cap means comprising a cup-shaped member and means to connect the cap means to the proximal end zone of the wall about said flash chamber comprising matching tapered surfaces.

3. The device as set forth in claim 1 wherein the cap means has an opening and includes a piece of bacterial filter material which is porous to air and non-porous to liquids fixed in spanning relation of said opening.

4. The device as set forth in claim 3 wherein said material is of a thin sheet of polyethylene fibers in mat form.

5. The device as set forth in claim 4 wherein the material is in sheet form and the margin of the filter material is fused to the cap means, and said cap means is of rigid plastic material.

6. The device as set forth in claim 3 wherein the material is TYVEK, a trademark of a commercially available product of the E.I. duPont de Nemours Co.

7. The device as set forth in claim 1 wherein said catheter comprises a generally tubular body of rubbery bendable material of a predetermined axial length fixed at one end to said adapter and the other end to said jacket.

8. The device as set forth in claim 7 wherein the oppositely extending ears of a substantially common size are provided on the tubular body at the said other end to stabilize the body and said body being adapted to be bowed intermediate its length by lifting its said one end.

9. The device as set forth in claim 1 wherein said jacket is provided with a rigid tubular segment of plastic telescoped over the proximal end zone of the jacket and means connecting the tubular segment to the tubular body.

10. The device as set forth in claim 1 wherein the proximal end of the rigid adapter is within said chamber a distance of at least one-quarter of an inch.

11. The improved catheter as set forth in claim 1 wherein a protective member is provided comprising an elongate cup-shaped receptacle to receive the needle and means to connect the member to the needle hub.

12. The device as set forth in claim 11 wherein the cup-shaped member is sized to receive the distal end of said shroud and includes stop means to limit insertion of said hub into said cup-shaped member.

* * * * *